(12) United States Patent
Nachum

(10) Patent No.: US 6,941,172 B2
(45) Date of Patent: Sep. 6, 2005

(54) METHOD AND DEVICE FOR RESTORING KIDNEY FUNCTION USING ELECTROMAGNETIC STIMULATION

(76) Inventor: Zvi Nachum, Rechov Rachel 9, Tiberias (IL)

( * ) Notice: Subject to any disclaimer, the term of this patent is extended or adjusted under 35 U.S.C. 154(b) by 182 days.

(21) Appl. No.: 10/298,095

(22) Filed: Nov. 18, 2002

(65) Prior Publication Data
US 2004/0098062 A1 May 20, 2004

(51) Int. Cl.$^7$ .................................... A61N 1/00
(52) U.S. Cl. ................. 607/40; 607/2; 607/72
(58) Field of Search ................. 607/1–156

(56) References Cited

U.S. PATENT DOCUMENTS 4,685,462 A * 8/1987 Olsen .................. 607/98
6,424,864 B1 * 7/2002 Matsuura .................. 607/3

* cited by examiner

Primary Examiner—Scott M. Getzow
(74) Attorney, Agent, or Firm—Mark M. Friedman

(57) ABSTRACT

A device for, and method of restoring kidney function, the method including the steps of: (a) providing a device including: (i) a conducting coil, and (ii) a signal generator, operatively connected to a power supply, for providing a plurality of electrical impulses to the coil; (b) disposing the conducting coil proximate to a kidney of a patient, and (c) delivering the electrical impulses conducting to the conducting coil, so as to produce an electromagnetic field, the electromagnetic field acting so as to stimulate the kidney and at least partially restore kidney function.

28 Claims, 5 Drawing Sheets

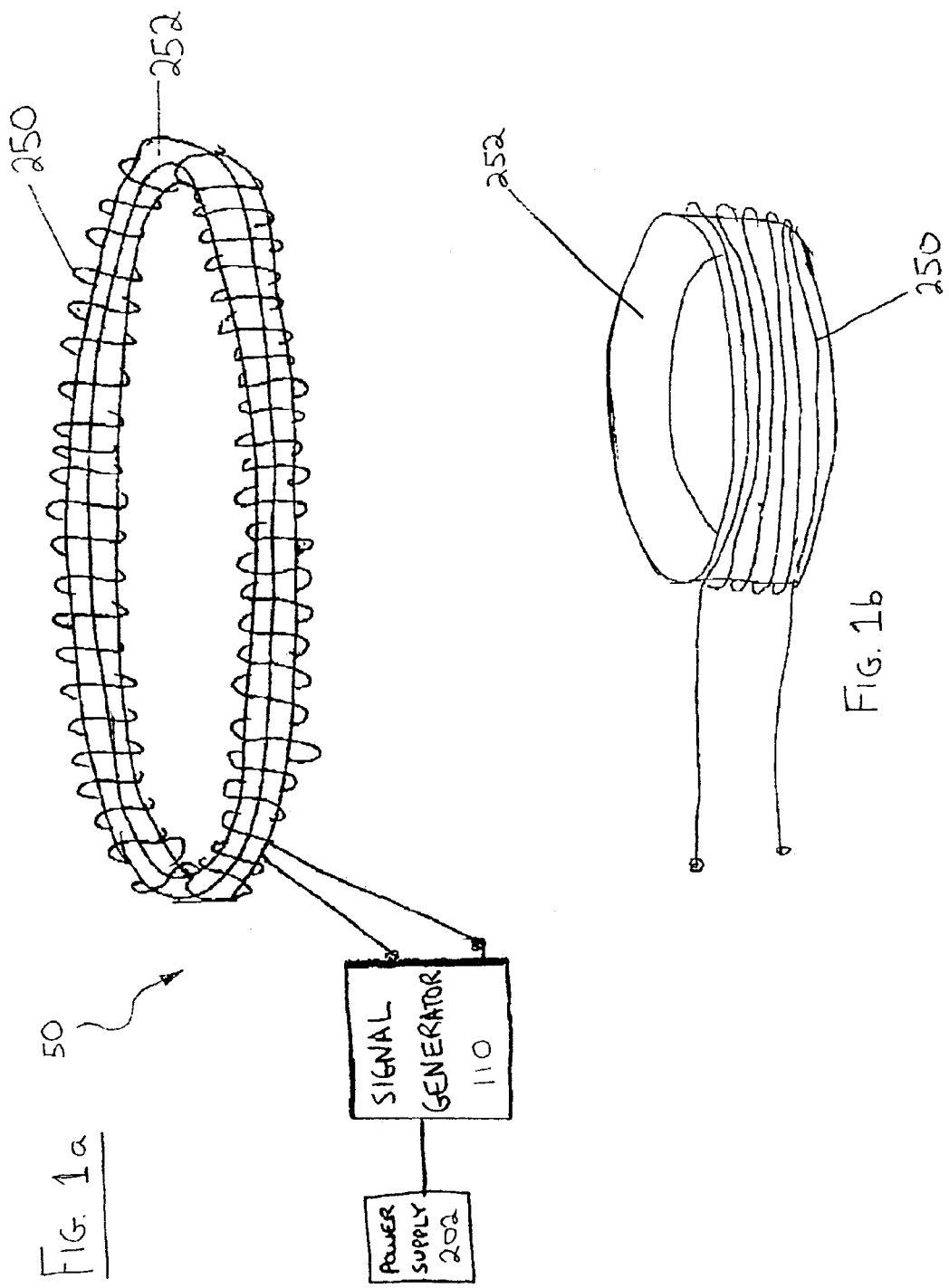

METHOD AND DEVICE FOR RESTORING KIDNEY FUNCTION USING ELECTROMAGNETIC STIMULATION

FIELD AND BACKGROUND OF THE INVENTION

The present invention relates to a method of and device for restoring kidney function, and more particularly, to a method of and device for restoring kidney function by means of electromagnetic stimulation.

As the restoration of kidney function is largely dependent on the cause of the kidney failure and on the state of the kidney tissue at the time the treatment is to be implemented, a brief overview of renal disease and renal failure is provided, along with a look at currently-known treatment procedures.

Kidney Failure

The distinction between acute and chronic renal failure is of cardinal importance. Chronic renal failure allows the body to adjust gradually, tolerating and compensating for the impaired function. Acute renal failure occurs rapidly, in a matter of hours or a few days, and therefore causes serious metabolic disruptions. During kidney failure, the kidneys stop filtering the body's metabolic waste products properly. These products collect in the blood, a condition known as uremia.

The most common causes of acute renal failure are shock or trauma (usually from blood loss), infection, and drug reactions, often in combination. Most cases now occur in the hospital, where the condition is easily and promptly diagnosed and acute kidney dialysis units are ready to begin treatment.

Chronic renal failure is usually caused by glomerulonephritis, diabetes mellitus, hypertension, amyloidosis (accumulation of protein and starch in various organs), and other conditions that cause long-term kidney damage.

Because acute failure occurs suddenly and usually involves the entire kidney, the flow of urine is usually suppressed. Even when the urine flow is very low, however, few people notice the change or realize its significance. When a toxic substance or a drug has caused acute failure, the symptoms of uremia manifest themselves before the person is aware of the problem. The acute and total loss of kidney function does not allow the body to compensate, and symptoms may develop within a few days, usually indicated by swelling of the feet, shortness of breath, or headache. These symptoms stem from the acute retention of salt and water, sharply raising blood pressure, altering brain metabolism, and congesting the heart and lungs. Without treatment, more serious problems appear, including hyperkalemia, a buildup in the blood of potassium that is usually excreted in the urine. Potassium buildup can cause heart rhythm irregularity or stop the heart completely, with potentially fatal results.

Unlike acute renal failure, chronic renal failure does not shut down the entire kidney at once. As some nephrons become diseased, others compensate, enlarging and assuming a portion of the lost function. Since the body has time to adjust, the symptoms of chronic failure differ considerably from those of acute failure and the adjustments are so successful that symptoms rarely are perceived until 90 to 95 percent of kidney function is lost. (At the same time, another illness, surgery, or a complication of hypertension may limit effective compensation.)

Symptoms usually appear so gradually, that patients adjust to them unconsciously: rising at night to pass urine, sleeping more to cope with fatigue, and avoiding stairs, hills, and lifting to offset breathlessness. Only when a minimally acceptable level of function has deteriorated, or when an acute episode is precipitated by a complication like stroke, heart failure, inflamed stomach, colon, or heart sac, do people seek medical attention.

Treatment

Acute renal failure is a medical emergency, but one that is rarely fatal, and is completely treatable with either medications or dialysis. Since acute failure today usually results from very serious disease elsewhere in the body, the outcome depends on the course of that disease. When the underlying kidney insult is corrected, most acute failure clears up in a few days with the help of medication. If a longer recovery period is necessary, dialysis may be needed until the kidneys heal, a process that may take 2 weeks to 2 months. Patients who do not respond to treatment may have to undergo long-term dialysis.

Dialysis

The most dramatic revolution in the treatment of chronic renal failure during the past 40 years has been the use of dialysis to treat chronic renal failure as well as acute renal failure. Although this may not seem revolutionary today, it represented a radically new idea in therapeutics.

Artificial kidneys generally filter the blood for 4 hours at a time, three times per week. Since these filters cannot perform any of the many metabolic functions of the kidney, full health cannot be truly restored, but most patients manage to maintain varied and useful lives despite the chronic state of disease produced by maintenance hemodialysis.

Dialysis patients must:

Adhere to rigid dialysis schedules

Restrict fluid intake and follow strictly controlled diets

Take daily medications

Endure anemia, abnormal bone metabolism, chronic uremia, and diminished sexual function Other possible complications of dialysis include high or low blood pressure, weakness, fatigue, cramps, weight loss, psychiatric disturbances, loss of nerve functions leading to muscle paralysis, and recurrent infections.

Still, for many the only alternative to dialysis is certain death, although at the time the first kidney machines were invented, few expected the human body to endure dialysis so well. From the time the artificial kidney was invented in 1946 until 1961, these machines were only used to tide over patients with acute renal failure who would eventually recover.

In the U.S.A. alone, over 90,000 people who would otherwise be dead are supported by kidney machines in hospitals, dialysis centers, or at home. The overall cost to the federal government (USA) for these programs is $3 billion annually.

An alternative to dialysis is transplantation. However, despite the newest medications, transplantation is inherently risky. The suppression and alteration of immunity—necessary during transplantation—creates unique problems and risks. During the first year, transplants result in death far more than does dialysis.

There is therefore a recognized need for, and it would be highly advantageous to have, a device for, and method of, averting the need for dialysis and kidney transplant, by restoring kidney function to kidneys in which the cells have stopped contributing, or contribute in a reduced fashion, to the overall functioning of the kidney. It would be of further advantage for the device and method to be painless, non-invasive, and safe for the user.

SUMMARY OF THE INVENTION

The present invention is a painless, non-invasive device for restoring kidney function to kidneys in which the cells are alive, but for various reasons, have stopped contributing, or contribute in a reduced fashion, to the overall functioning of the kidney. The treatment is effected by the application of an electromagnetic field external to the kidney. The application of an external electromagnetic field can be performed as a series of treatments that concludes with restoration of (or at least improved) kidney function.

According to one aspect of the present invention there is provided a method of restoring kidney function, the method including the steps of: (a) providing a device including: (i) a conducting coil, and (ii) a signal generator, operatively connected to a power supply, for providing a plurality of electrical impulses to the coil; (b) disposing the conducting coil proximate to a kidney of a patient, and (c) delivering the electrical impulses conducting to the conducting coil, so as to produce an electromagnetic field, the electromagnetic field acting so as to stimulate the kidney and at least partially restore kidney function.

According to another aspect of the present invention there is provided a device for restoring kidney function, the device including: (a) a conducting coil, designed and configured for disposing proximate to a kidney of a patient and (b) a signal generator, operatively connected to a power supply, for providing a plurality of electrical impulses to the conducting coil, the conducting coil and the signal generator designed and configured so as to produce an electromagnetic field in a vicinity of the coil, so as to stimulate the kidney and at least partially restore the kidney function.

According to further features in the described preferred embodiments, the signal generator includes at least one capacitor for delivering current, upon demand, to the conducting coil.

According to further features in the described preferred embodiments, the at least one capacitor for delivering current is a plurality of capacitors.

According to further features in the described preferred embodiments, the signal generator includes a central processing unit (CPU) for operatively controlling the least one capacitor so as to produce the electromagnetic field.

According to further features in the described preferred embodiments, the electromagnetic field varies with time, the electromagnetic field having a magnetic flux density characterized by a bi-phasic waveform.

According to further features in the described preferred embodiments, the electromagnetic field varies with time, the electromagnetic field having a magnetic flux density characterized by a mono-phasic waveform.

According to further features in the described preferred embodiments, the electromagnetic field varies with time, the electromagnetic field having a peak magnetic flux density of 1–40 millitesla.

According to further features in the described preferred embodiments, the electromagnetic field has a peak magnetic flux density of 10–20 millitesla.

According to further features in the described preferred embodiments, the electromagnetic field varies with time, the electromagnetic field having a magnetic flux density characterized by a series of waveform pulses, and a pulse rate of the pulses, and wherein the pulse rate is within a range of 0.05–100 pulses per minute.

According to further features in the described preferred embodiments, the pulse rate is within a range of 3–30 pulses per minute.

According to further features in the described preferred embodiments, the electromagnetic field varies with time, the electromagnetic field having a magnetic flux density characterized by a series of waveform pulses, and wherein a time between pulses is less than 0.3 minutes.

According to further features in the described preferred embodiments, the device further includes: (iii) a substantially non-conducting support for the conducting coil.

According to further features in the described preferred embodiments, the conducting coil is further designed and configured to fit around a torso of the patient.

According to further features in the described preferred embodiments, the non-conducting support and the coil form a unit, the support braci the unit self-supporting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1a is a schematic illustration of the device according to the present invention;

FIG. 1b is a schematic illustration of an alternative configuration of the coil illustrated in FIG. 1a;

DESCRIPTION OF THE PREFERRED EMBODIMENTS

Figure 1C:
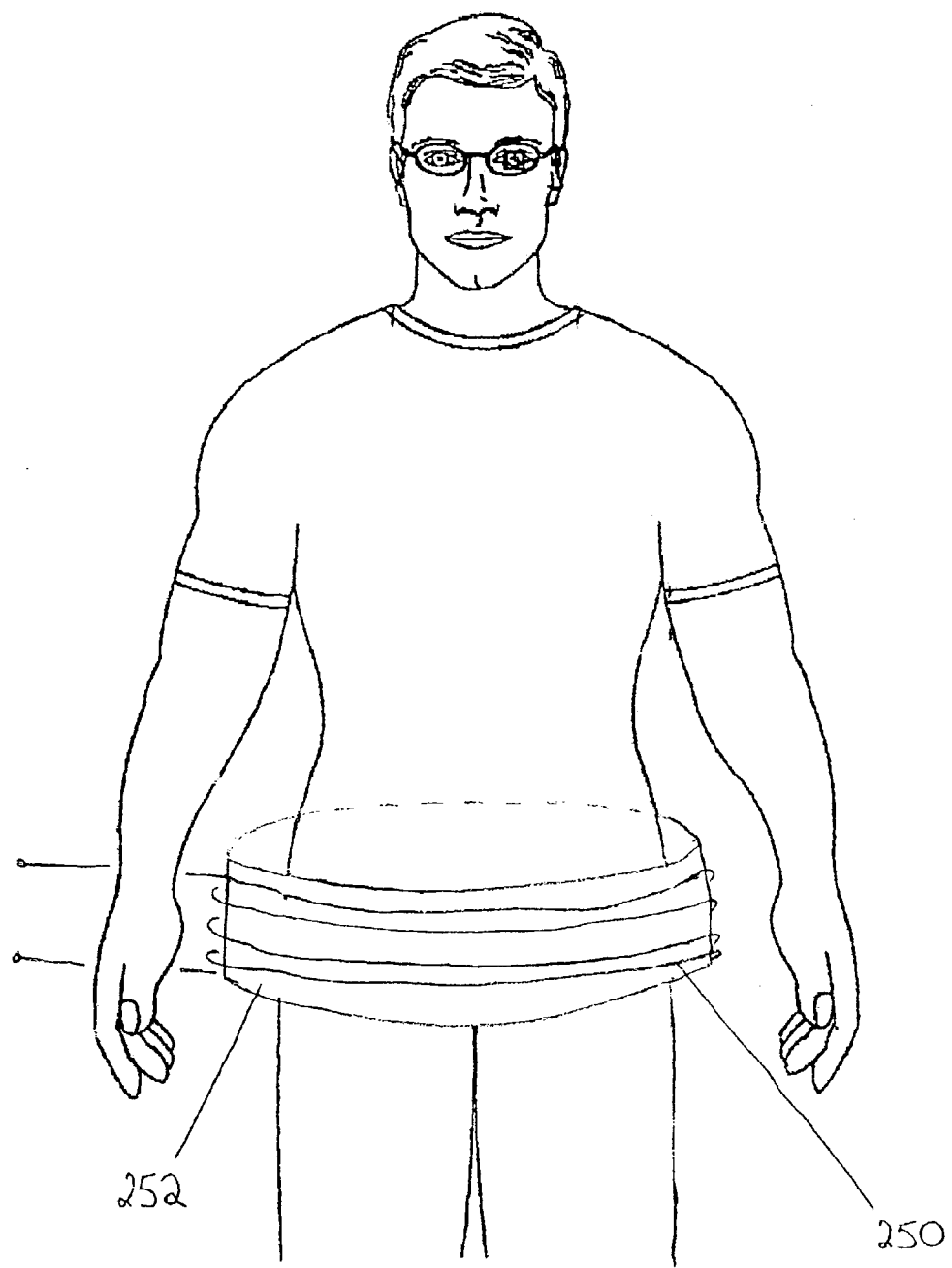
FIG. 1c is a schematic illustration of the coil of FIG. 1b, disposed around the torso of a patient.

Before explaining at least one embodiment of the invention in detail, it is to be understood that the invention is not limited in its application to the details of construction and the arrangement of the components set forth in the following description or illustrated in the drawing. The invention is capable of other embodiments or of being practiced or carried out in various ways. Also, it is to be understood that the phraseology and terminology employed herein is for the purpose of description and should not be regarded as limiting.

FIG. 1a is a schematic illustration of the system according to the present invention. The system 50 includes at least one signal generator 110 operatively connected to a power supply 202 and to a coil 250. Within coil 250 is an annular support 252, preferably made from a substantially non-conducting material such as plastic. With the power supplied by power supply 202, the signal generator 110 generates electrical impulses that are passed through coil 250. As a result, an electromagnetic field is generated within coil 250, and in the region surrounding coil 250. A voltage of up to 30 Volts is preferably applied.

An alternative configuration of coil 250, wound around support 252, is provided by way of example in FIG. 1b. Support 252 and coil 250 preferably form a self-supporting or self-standing unit, as shown, inter alia, in FIG. 1b.

Upon placing coil 250 in the vicinity of the kidney, the electromagnetic radiation, the pattern of which is determined by the form, frequency, and intensity of the signals provided to the coil, acts upon the kidney and results in the stimulation of the affected area thereof.

In a preferred embodiment, shown in FIG. 1c, coil 250 is designed so as to fit around the torso of a patient. Although it is preferable for the skin tissue in the vicinity of the kidney to be substantially enveloped by coil 250, it is possible to place coil 250 in proximity to skin surface external to the kidney (i.e., without enveloping the body) so as to expose the kidney to the electromagnetic field produced by coil 250.

Figure 2:
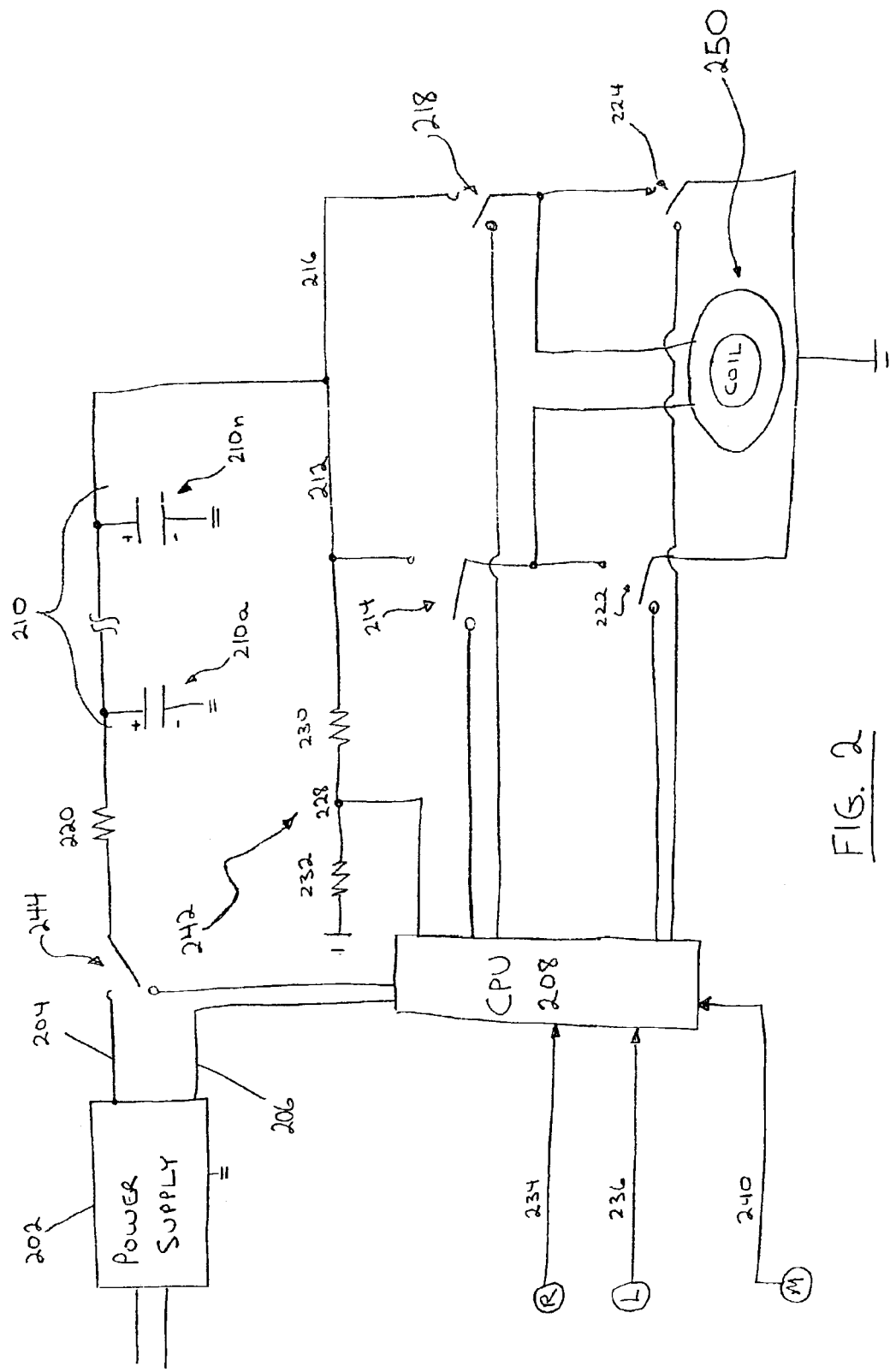
FIG. 2 is a schematic wiring diagram of the stimulation device of the present invention.

A schematic wiring diagram of the device of the present invention is provided in FIG. 2. Power supply 202 is equipped with a high voltage line 204 and a low voltage line 206. Low voltage line 206 supplies power to CPU 208. High voltage line 204 supplies power to capacitor bank 210, which contains a plurality of capacitors 210a–n for delivering, upon demand, current to coil 250 so as to produce an electromagnetic field. Typically, capacitor bank 210 includes at least ten capacitors. The power is preferably supplied to capacitor bank 210 via resistor 220, which serves to slow/regulate charging to capacitor bank 210.

The current delivered from capacitor bank 210 can be conducted via line 212 and switch 214, or via line 216 and switch 218, to coil 250. Switches 214 and 218, as well as switches 222 and 224, are controlled by CPU 208. Inputs to CPU 208 include a signal pulse rate input 234, a signal level input 236, both of which can be pre-set or pre-programmed, and a manual input 240 for manually discharging capacitor bank 210 so as to deliver an electrical impulse to coil 250.

Also inputting to CPU 208 is a signal from current indicator (or sampler) 242. As shown by way of example, current indicator 242 includes branch point 228, having a resistor 230 electrically connected to capacitor bank 210 on one side, and a second resistor 232 electrically connected to branch point 228 on the opposite side. Current indicator 242 provides feedback to CPU 208 on the amount of current flowing out of capacitor bank 210 in the direction of coil 250, information that is used by CPU 208 to control the system so as to produce an electromagnetic field having the desired properties.

For example, based on the feedback provided by current indicator 242, CPU 208 operates a switch 244, disposed on high voltage line 204, so as to control the charging of capacitor bank 210.

Figure 3A:
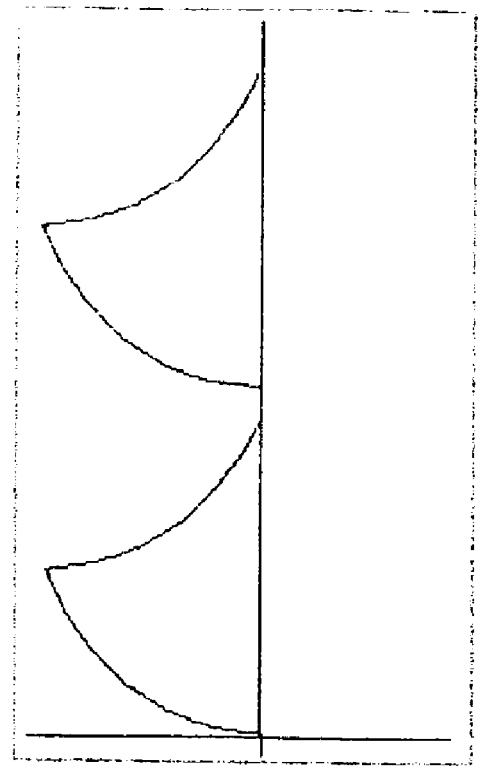
FIGS. 3a and 3b provide typical electromagnetic waveforms for stimulation of the kidney, according to the present invention.
Figure 3B:
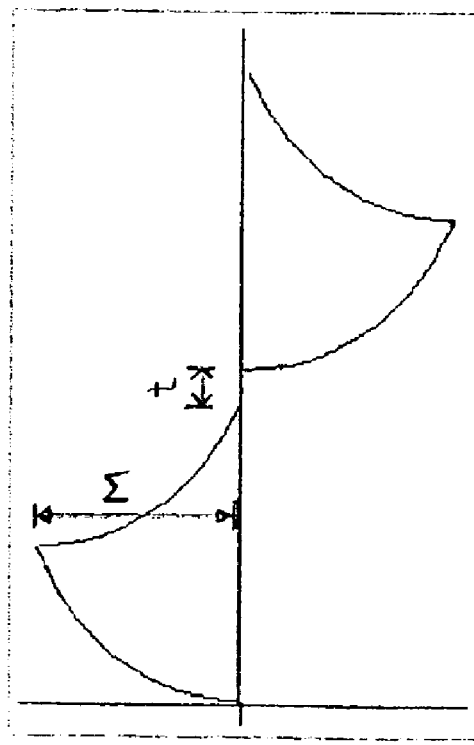

Typical electromagnetic waveforms for stimulation of the kidney are presented in FIGS. 3a and 3b. Magnetic flux density is plotted on the y axis, as a function of time. A bi-phasic waveform is provided in FIG. 3a; a mono-phasic waveform is provided in FIG. 3b.

The maximum value of the magnetic flux density, M, is 1–40 millitesla. More preferably, the maximum value of the magnetic flux density, M, is 5–40 millitesla, and most preferably, between 10 and 20 millitesla. The pulse rate is preferably 0.05–100 pulses per minute. Presently, a more preferred pulse rate is 0.5–30 pulses per minute. The time between pulses, t, is less than 10 seconds, preferably less than 3 seconds. Depending on the specific design and configuration of signal generator 110, the time between pulses may be heavily dependent on the magnitude (peak) of the previous pulse.

The device and method of the present invention appear to be most effective in treating kidney failure due to trauma. Kidney failure due to trauma is acute, and is generally reversible, at least during the initial stages. Without wishing to be limited by theory, it is believed that a static charge builds up within the tissues of the kidney, for reasons that are not yet fully understood. This static charge inhibits proper functioning of the kidney. As long as no significant irreversible damage has been caused to the kidney, the kidney can be stimulated into regaining normal performance by clearing the static charge within the tissues of the kidney by application of an electromagnetic field using the device and method of the present invention.

EXAMPLE 1

A patient suffering from traumatic, acute renal failure was fitted with the device of the present invention, as shown in FIG. 1c. Using the device, an electromagnetic field was produced in the vicinity of the kidneys, the field being characterized by a pulse rate of approximately 1 pulse per minute.

Figure 4:
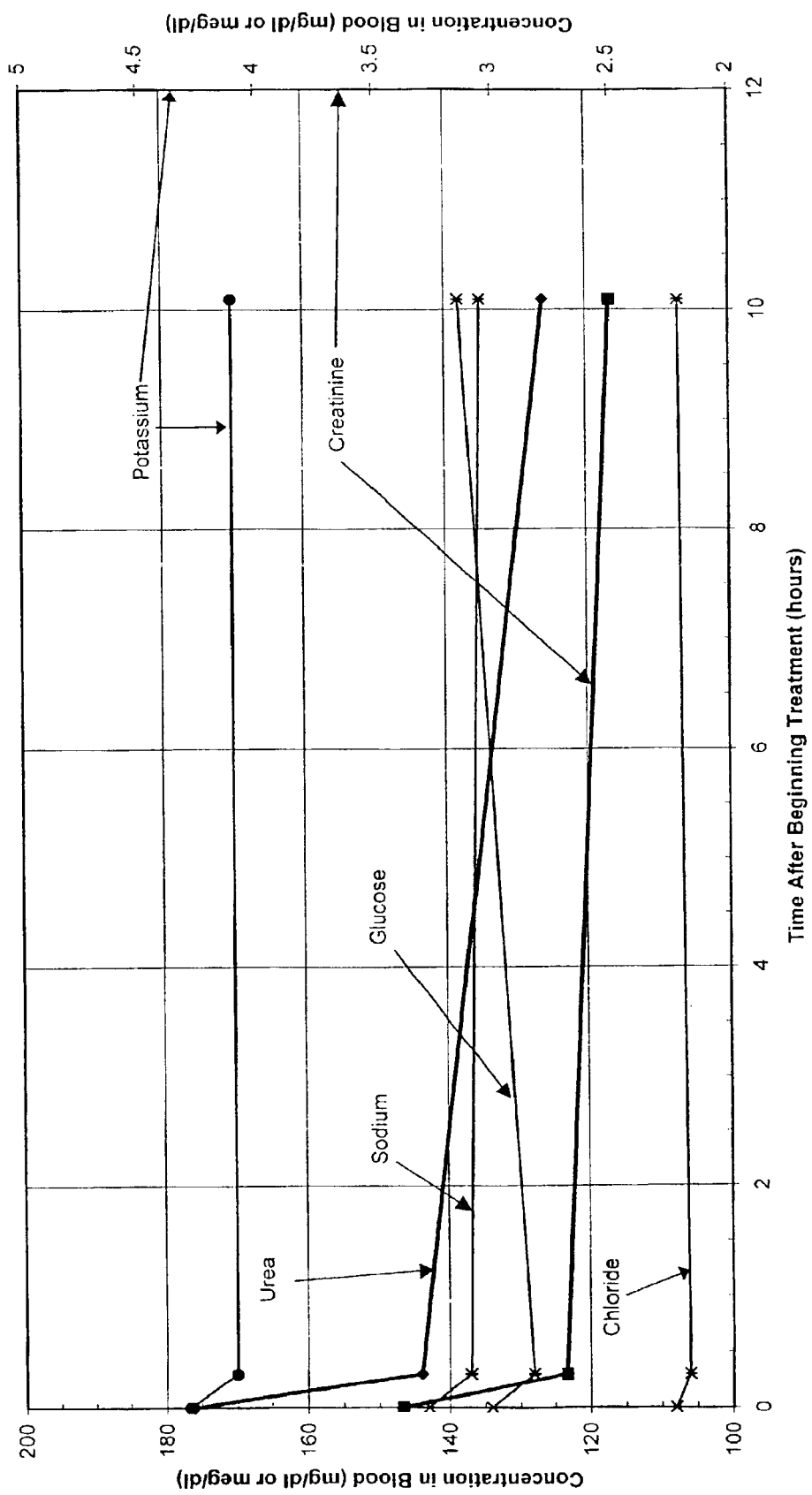
FIG. 4 is a graph illustrating the decrease in urea and creatinine values in the bloodstream of a patient, following the administering of a sequence of electromagnetic pulses, in accordance with the device and method of the present invention.

Samples were taken from the bloodstream of the patient immediately before initiation of the electromagnetic field, immediately following the administering of the electromagnetic pulses, and about 10 hours thereafter. The results of the blood sampling are provided in Table 1, and are presented graphically in FIG. 4.

TABLE 1

| | | CONCENTRATION IN BLOOD | | |
|---|---|---|---|---|
| SUBSTANCE IN BLOOD | UNITS | TIME = 0 (Beginning of Treatment) | TIME = 0.3 hours (Immediately After Treatment) | TIME = 10.1 hours |
| UREA | mg/dl | 176 | 144 | 126 |
| CREATININE | mg/dl | 3.4 | 2.7 | 2.5 |
| GLUCOSE | mg/dl | 134 | 128 | 138 |
| POTASSIUM | meg/dl | 4.3 | 4.1 | 4.1 |
| SODIUM | meg/dl | 143 | 137 | 135 |
| CHLORIDE | meg/dl | 108 | 106 | 107 |

The concentrations of urea and creatinine in the bloodstream are known indicators of kidney performance. Whereas the concentrations of other substances in the blood—glucose, potassium, sodium, and chloride, remain essentially constant, it is evident that an appreciable decrease in the urea and creatinine levels in the bloodstream has been achieved. Within 20 minutes, the urea and creatinine levels decreased by about 20%. After 10 hours, and without additional electromagnetic applications, the urea and creatinine levels decreased by an additional 10%, indicating that the kidneys continue to regain performance well after the electromagnetic application has been terminated.

Although the invention has been described in conjunction with specific embodiments thereof, it is evident that many alternatives, modifications and variations ill be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of restoring kidney function to a patient suffering from acute renal failure, the method comprising the steps of:
   (a) providing a device including:
      (i) a conducting coil, and
      (ii) a signal generator, operatively connected to a power supply, for providing a plurality of electrical impulses to said coil;
   (b) disposing said conducting coil proximate to a kidney of the patient suffering from acute renal failure, and
   (c) delivering said electrical impulses conducting to said conducting coil, so as to produce an electromagnetic field,
   said electromagnetic field acting so as to at least partially restore the kidney function.

2. The method of claim 1, wherein said electromagnetic field varies with time, said electromagnetic field having a peak magnetic flux density of at least 1 millitesla.

3. The method of claim 1, wherein said electromagnetic field varies with time, said electromagnetic field having a magnetic flux density characterized by a series of waveform pulses, and a pulse rate of said pulses, and wherein said pulse rate is within a range of 0.05–100 pulses per minute.

4. The method of claim 1, wherein said signal generator includes at least one capacitor for delivering current, upon demand, to said conducting coil, the method further comprising the step of:
   (d) operatively controlling said least one capacitor so as to produce said electromagnetic field.

5. The method of claim 1, wherein said electromagnetic field varies with time, said electromagnetic field having a magnetic flux density characterized by a bi-phasic waveform.

6. The method of claim 1, wherein the acute renal failure is an acute renal failure resulting from trauma.

7. The method of claim 1, wherein the acute renal failure is an acute renal failure resulting from infection.

8. The method of claim 1, wherein the acute renal failure is an acute renal failure resulting from a drug reaction.

9. A method of restoring kidney function to a patient suffering from acute renal failure, the method comprising the steps of:
   (a) providing a device including:
      (i) a conducting coil, and
      (ii) a signal generator, operatively connected to a power supply, for providing a plurality of electrical impulses to said coil;
   (b) disposing said conducting coil proximate to a kidney of the patient, and
   (c) delivering sail electrical impulses conducting to said conducting coil, so as to produce an electromagnetic field, so as to at least partially restore the kidney function,
   wherein said electromagnetic field varies with time and has a peak magnetic flux density of at least 1 millitesla.

10. The method of claim 9, wherein said electromagnetic field has a peak magnetic flux density of at least 10 millitesla.

11. The method of claim 9, wherein said electromagnetic field has a magnetic flux density characterized by a series of waveform pulses, and a pulse rate of said pulses, and wherein said pulse rate is within a range of 0.05–100 pulses per minute.

12. The method of claim 9, wherein said electromagnetic field has a magnetic flux density characterized by a series of waveform pulses, and wherein a time between pulses is less than 0.3 minutes.

13. The method of claim 9, wherein said electromagnetic field has a magnetic flux density characterized by a bi-phasic waveform.

14. A method of restoring kidney function to a patient suffering from acute renal failure, the method comprising the steps of:
   (a) providing a device including:
      (i) a conducting coil, and
      (ii) a signal generator, operatively connected to a power supply, for providing a plurality of electrical impulses to said coil;
   (b) disposing said conducting coil proximate to a kidney of the patient, and
   (c) delivering said electrical impulses conducting to said conducting coil, so as to produce an electromagnetic field, so as to at least partially restore the kidney function,
   wherein said electromagnetic field varies with time, said electromagnetic field having a magnetic flux density characterized by a series of waveform pulses, and a pulse rate of said pulses, and wherein said pulse rate is within a range of 0.05–100 pulses per minute.

15. The method of claim 14, wherein said pulse rate is within a range of 3–30 pulses per minute.

16. The method of claim 14, wherein said electromagnetic field has a magnetic flux density characterized by a monophasic waveform.

17. The method of claim 14, wherein said electromagnetic field varies with time, said electromagnetic field having a magnetic flux density characterized by a series of waveform pulses, and wherein a time between pulses is less than 0.3 minutes.

18. A device for restoring kidney function to a patient suffering from acute renal failure, the device comprising:
   (a) a conducting coil, designed and configured for disposing proximate to a kidney of the patient, and
   (b) a signal generator, operatively connected to a power supply, for providing a plurality of electrical impulses to said conducting coil,
   said conducting coil and said signal generator designed and configured so as to produce an electromagnetic field in a vicinity of said coil, said electromagnetic field having a peak magnetic flux density of at least 1 millitesla, so as to stimulate said kidney and at least partially restore the kidney function.

19. The device of claim 18, wherein said conducting coil and said signal generator are designed and configured such that said electromagnetic field varies with time.

20. The device of claim 18, wherein said signal generator is designed and configured such that said electromagnetic field has a peak magnetic flux density of at least 10 millitesla.

21. The device of claim 18, wherein said conducting coil is further designed and configured to fit around a torso of said patient.

22. The device of claim 18, wherein said signal generator includes at least one capacitor for delivering current, upon demand, to said conducting coil.

23. The device of claim 22, wherein said signal generator includes a central processing unit (CPU) for operatively controlling said least one capacitor so as to produce said electromagnetic field.

24. The device of claim 18, wherein said signal generator is further designed and configured to produce a bi-phasic waveform.

25. A device for restoring kidney function to a patient suffering from acute renal failure, the device comprising:

(a) a conducting coil, designed and configured for disposing proximate to a kidney of the patient, and (b) a signal generator, operatively connected to a power supply, for providing a plurality of electrical impulses to said conducting coil, said conducting coil and said signal generator designed and configured so as to produce an electromagnetic field in a vicinity of said coil, said electromagnetic field varying with time, said electromagnetic field having a magnetic flux density characterized by a series of waveform pulses, and a pulse rate of said pulses, and wherein said pulse rate is within a range of 0.05–100 pulses per minute.

26. The device of claim 25, wherein said signal generator is designed and configured such that said pulse rate is within a range of 3–30 pulses per minute.

27. The device of claim 25, wherein said electromagnetic field has a magnetic flux density characterized by a series of waveform pulses, said signal generator designed and configured such that a time between pulses is less than 0.3 minutes.

28. The device of claim 25, wherein said electromagnetic field has a magnetic flux density characterized by a monophasic waveform.

* * * * *